US00PP15911P2

(12) United States Plant Patent
Bak et al.

(10) Patent No.: US PP15,911 P2
(45) Date of Patent: Aug. 9, 2005

(54) ***GUZMANIA* PLANT NAMED OF 'COMBI'**

(50) Latin Name: ***Guzmania* hybrid**
Varietal Denomination: Combi

(75) Inventors: Elly Bak, Rijsenhout (NL); Nicolaas D. M. Steur, Oude Niedorp (NL)

(73) Assignee: Corn Bake B.V. (NL)

( * ) Notice: Subject to any disclaimer, the term of this patent is extended or adjusted under 35 U.S.C. 154(b) by 88 days.

(21) Appl. No.: 10/788,384

(22) Filed: Mar. 1, 2004

(51) Int. Cl.[7] ..... A01H 5/00
(52) U.S. Cl. ..... Plt./371
(58) Field of Search ..... Plt./371

*Primary Examiner*—Kent Bell
(74) *Attorney, Agent, or Firm*—Foley & Lardner, LLP

(57) ABSTRACT

A new and distinct *Guzmania* Plant Named 'Combi' particularly characterized by its solid, tenable, long lasting habit; having compact plant habit; wide leaves; superior bract production; and compound purple inflorescence.

2 Drawing Sheets

Latin name of the genus and species of the plant claimed: *Guzmania* hybrid.
Variety denomination: Combi.

BACKGROUND OF THE INVENTION

The present invention relates to a new and distinct cultivar of *Guzmania* plant, botanically known as *Guzmania* hybrid, hereinafter referred to by the cultivar name 'Combi'.

*Guzmania* is predominantly epiphytic with a few terrestrial species and is native to the tropics. For the most part, species vary in diameter from 7 or 8 inches to 3 or 4 feet and have rosettes of glossy, smooth-edged leaves. Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Desirably, the plants are shaded from direct sunlight, and during the spring to autumn period, the central vase-like part of the leaf rosette is desirably filled with water. Leaves of *Guzmania* are usually formed as basal rosettes, which are stiff and entire and in several vertical ranks. *Guzmania* plants have terminal spikes or panicles which are often bracted with petals united in a tube about as long as the calyx.

This new hybrid *Guzmania* 'Combi' is a naturally occurring whole plant mutation of *Guzmania* 'Luna' (unpatented) of the family Bromeliaceae, and was discovered by the inventors, Elly Bak and Nicolaas D.M. Steur. *Guzmania* 'Combi' flowered for the first time in 1999 in Assendelft, the Netherlands.

Asexual reproduction of the new cultivar through tissue culture was first performed in 1993 Assendelft, The Netherlands and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Combi' which in combination distinguish this *Guzmania* as a new and distinct cultivar:

1. Solid, tenable, long lasting habit;
2. Compact plant habit;
3. Wide leaves;
4. Superior bract production; and
5. Compound purple inflorescence.

The closest comparison cultivar is *Guzmania* 'Luna' (unpatented). The most important differences between 'Luna' and 'Combi' are their shape and size. The inflorescence of *Guzmania* 'Combi' is more compact and the leaves are wider than those of *Guzmania* 'Luna'.

*Guzmania* 'Combi' is not tested under all available environmental conditions like temperature, light intensity, day length, fertilizers and humidity.

BRIEF DESCRIPTION OF THE DRAWING

The accompanying photographic illustrations show the new cultivar with colors as true as possible with photographic reproductions.

The first photographic drawing shows a close-up of the bracts of the new cultivar 'Combi'.

The second photographic drawing shows the new cultivar 'Combi' in its entirety.

DETAILED BOTANICAL DESCRIPTION

The following observations, measurements and values describe the new cultivar at two years old as grown in Assendelft, The Netherlands, under conditions which closely approximate those generally used in commercial practice. Observations, measurements and descriptions of *Guzmania* 'Combi' were done under Dutch greenhouse conditions. Color references are made to The Royal Horticultural Society Colour Chart (R.H.S.), except where general colors of ordinary significance are used.

Plant:

*Form.*—Funnel form rosette.
*Height.*—Approximately 40–45 cm high (flowering).
*Growth habit.*—Stemless.
*Diameter.*—Approximately 60 cm.

Foliage:

*Size of leaf.*—Length: approximately 45 cm; width: approximately 4–5 cm.

*Shape of leaf.*—Lanceolate.

*Surface texture.*—Smooth.

*Color.*—Upperside: RHS 147A. Underside: RHS 147 B. (Leaf color dependent on environmental conditions).

Bracts:

*Scape bracts.*—Length: Lowest bract approximately 20 cm, to approximately 12 cm just below the primary bracts. Width: Approximately 4–4.5 cm. Shape: Lanceolate; acute apex; margin entire. Number: Approximately 12. Texture: Smooth. Color: RHS 187 D (both surfaces) with green tips, RHS 139 A.

*Primary bracts.*—Length: Lowest bract approximately 12 cm, to approximately 8 cm at the top. Width: Approximately 4–5 cm. Shape: Lanceolate; acute apex; margin entire. Number: Approximately 8. Texture: Smooth. Color: RHS 187 D (both surfaces).

*Floral bracts.*—Length: Approximately 2–5 cm. Width: Approximately 1 cm. Shape: Lanceolate; acute apex; margin entire. Number: About 7 per branch. Texture: Smooth. Color: Whitish-transparent with a touch of purple, RHS 187D.

Flowers:

*Borne.*—Erect.

*Shape of inflorescence.*—Densely bipinnate.

*Size of inflorescence on stalk.*—Approximately 9 cm.

*Diameter of inflorescence.*—Approximately 20 cm.

*Individual petals: (disposed within the inflorescence).*—Length: Approximately 5 cm. Width: Approximately 0.5 cm. Quantity: Approximately 45 flowers depending on the size of the plant. Color: Whitish to transparent and yellow RHS 7B (flowers are disposed within the inflorescence).

Time of blooming: A fully grown plant can produce an inflorescence containing approximately 45 flowers and can bloom anytime throughout the year starting approximately 15 weeks after natural induction or induction with acetylene. The total length of blooming of the whole inflorescence is 5 weeks.

Reproductive organs:

*Ovaries.*—Superior.

*Pistil.*—1 per flower, RHS 158A.

*Style.*—4.5 cm.

*Stamens.*—6 in number.

*Pollen.*—Not produced.

*Seed characteristics.*—The plant is a sterile hybrid, therefore no fruit or seed.

Disease/pest resistance/susceptibility: No observations made to date.

We claim:

1. A new and distinct *Guzmania* plant named 'Combi', as described and illustrated herein.

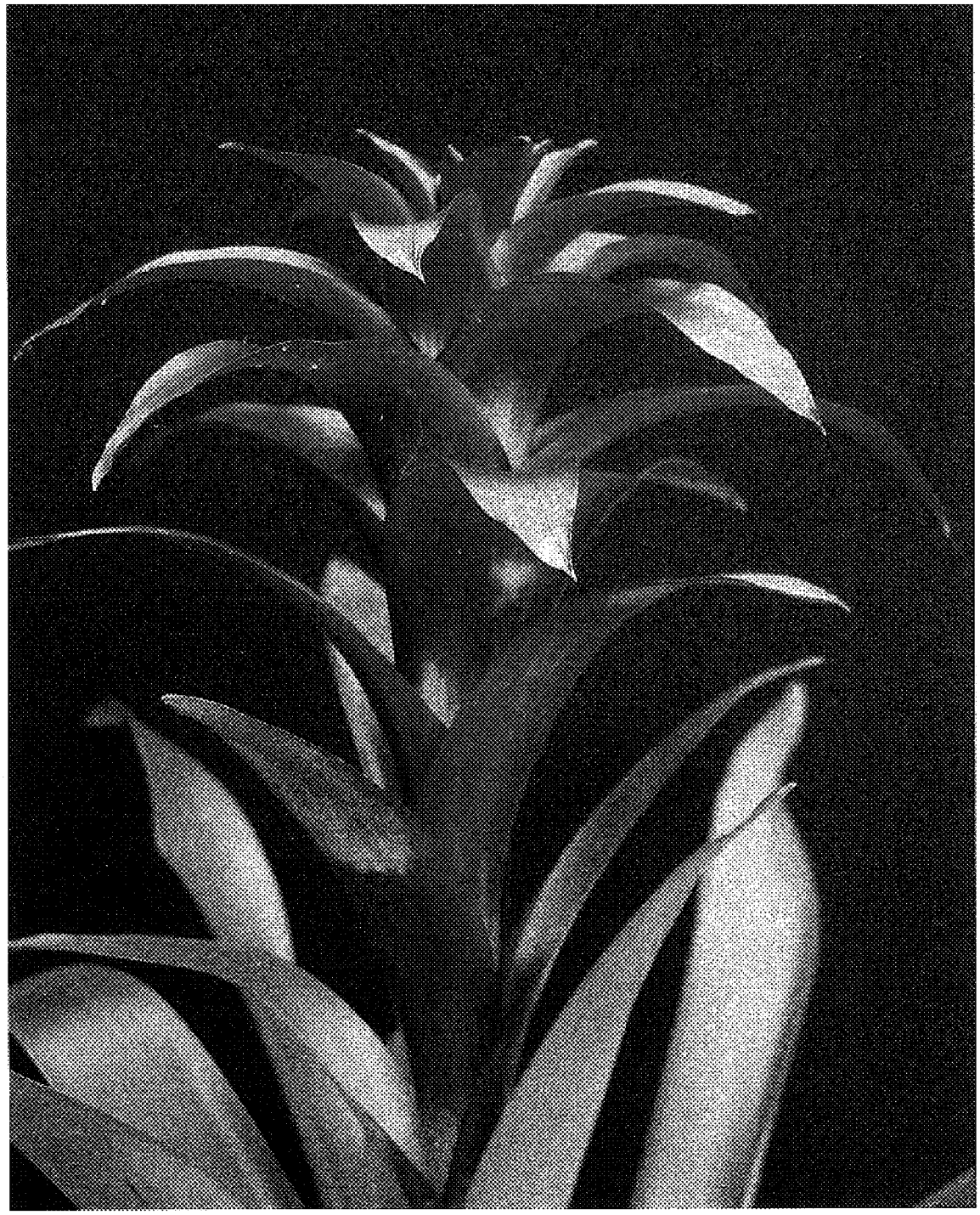

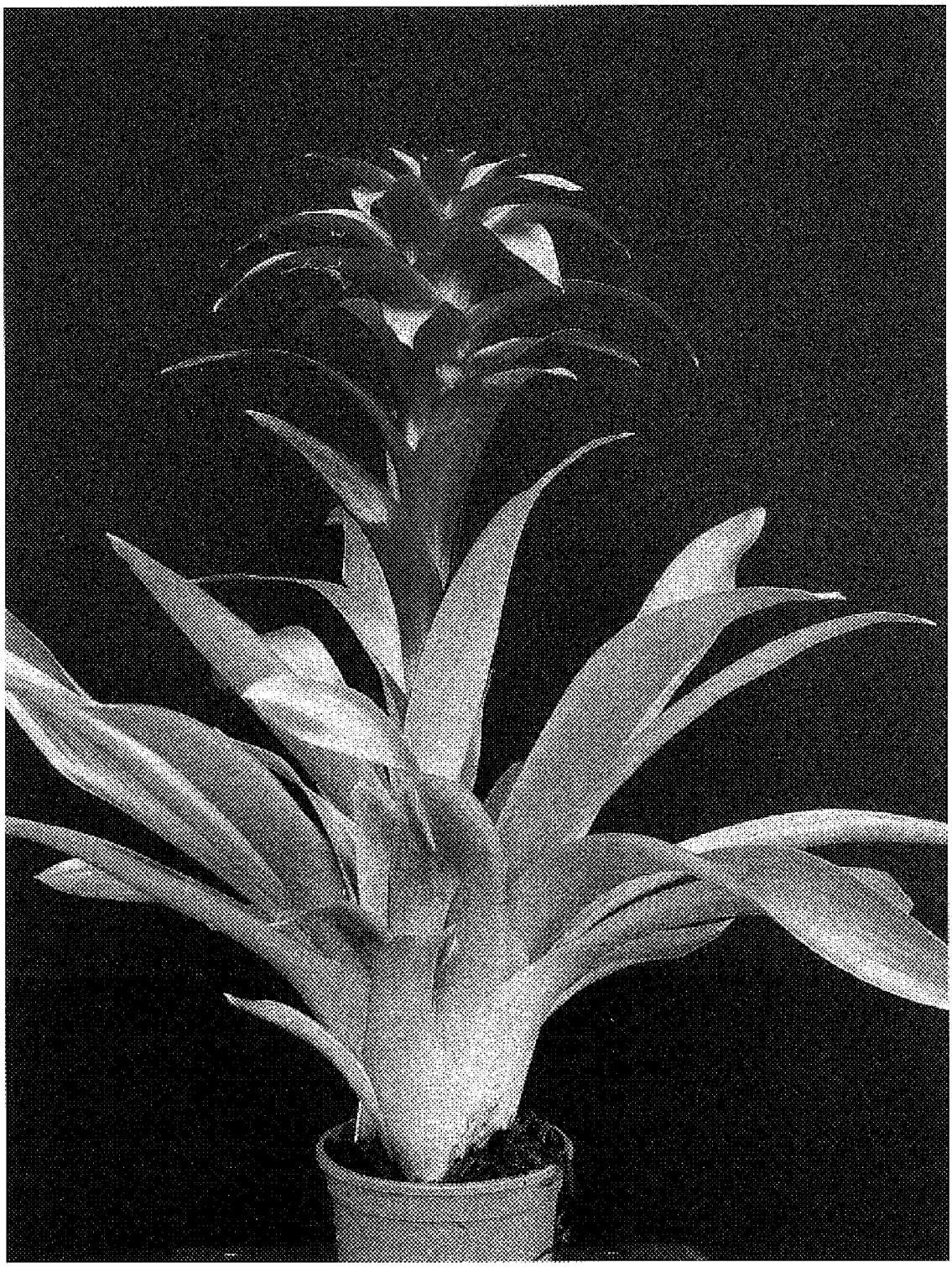

* * * * *